United States Patent [19]
Keith et al.

[11] Patent Number: 6,126,609
[45] Date of Patent: Oct. 3, 2000

[54] APPARATUS FOR TAKING BLOOD SAMPLES FROM A PATIENT

[75] Inventors: Hunt H. Keith, Rembert; Scott Winfield Rumph, III, Sumter, both of S.C.

[73] Assignee: Keith & Rumph Inventors, Inc., Dublin, Ga.

[21] Appl. No.: 09/197,979

[22] Filed: Nov. 23, 1998

[51] Int. Cl.[7] ................................................ A61B 5/00
[52] U.S. Cl. .......................................................... 600/528
[58] Field of Search .............................. 600/573, 575, 600/578, 579, 584

[56] References Cited

U.S. PATENT DOCUMENTS

| | | |
|---|---|---|
| 3,616,789 | 11/1971 | Grabhorn . |
| 3,633,566 | 1/1972 | Grabhorn . |
| 3,765,402 | 10/1973 | Grabhorn . |
| 3,952,729 | 4/1976 | Libman et al. . |
| 4,077,395 | 3/1978 | Woolner . |
| 4,326,519 | 4/1982 | D'Alo et al. . |
| 4,696,309 | 9/1987 | Stephan . |
| 4,951,685 | 8/1990 | Blair ........................................ 600/573 |
| 4,976,271 | 12/1990 | Blair . |
| 5,067,532 | 11/1991 | Lang et al. . |
| 5,143,084 | 9/1992 | Macemon et al. . |
| 5,241,969 | 9/1993 | Carson et al. . |
| 5,507,299 | 4/1996 | Roland . |

Primary Examiner—Max Hindenburg
Attorney, Agent, or Firm—Dority & Manning, P.A.

[57] ABSTRACT

A device for use with conventional blood receptacle assemblies provides increased safety and stability for blood collecting operations. The blood drawing device includes a holding element for securing a blood collecting assembly and a clamping mechanism for clamping a blood sampling tube. A sliding mechanism is provided for sliding the blood sampling tube into engagement with the blood collecting assembly. In an alternative embodiment, the blood drawing device may be configured to include a carriage assembly moveably attached to a base and holding a plurality of blood tubes for blood collection. A servo motor moves the carriage assembly relative to the base. A mechanism reciprocates the blood tube between a first and second position such that movement of the tube causes the tube to engage a needle inside the blood collecting assembly. The device may further include sensors for detecting the fill level of the tube and a sensor that detects the insertion of the tube into the opening of the carriage assembly to activate the servo motor to reciprocally move the tube.

31 Claims, 7 Drawing Sheets

APPARATUS FOR TAKING BLOOD SAMPLES FROM A PATIENT

BACKGROUND OF THE INVENTION

The present invention is directed to the field of obtaining blood samples from a living patient and more particularly to apparatus suitable for use with conventional blood receptacle assemblies and double-ended needles.

Various devices and methods have been developed for withdrawing blood from a patient. FIG. 1 shows one such blood receptacle assembly A, along with a first embodiment of the present invention to be described below. Assembly A includes two parts: blood collecting assembly B and blood sampling tube C. Tube C is a standard blood sampling tube, and has a rubber stopper D in the opening E of tube C. Blood collecting assembly B includes a first housing F including a hollow needle G. Housing F is attached by flexible tubing H to a second housing I having a second needle J. First needle G punctures the skin and underlying vein of the patient (not shown). Rubber stopper D is inserted into housing I so that second needle J extends through stopper D into the tube C. (As shown in FIG. 1, tube C is in a retracted position relative to housing I in which needle J does not penetrate stopper D). One such device for withdrawing blood is known as a "VACUTAINER," and is available from Becton-Dickenson, although others are also available.

In use, blood travels from the patient to the tube C via needle G, flexible tubing H, and needle J. Often, more than one sample of blood is required, each sample being placed in a separate blood sampling tube C which may contain one of a variety of preparations to facilitate a particular analytical procedure. Such preparations may include, for example, preservatives, anti-coagulants, and the like.

Using conventional blood sampling devices, a venipuncturist must stabilize the first needle puncturing the vein while simultaneously manipulating the blood sampling tube or tubes into the housing and into engagement with the second needle. Occasionally, the process of engaging blood sampling tube C with second needle J causes first needle G, in contact with the patient's vein, to inadvertently dislodge or puncture the other side of the patient's vein. In addition to increasing the painfulness of the procedure and possibly contributing to hematoma formation, dislodging the needle or puncturing the other side of the vein may necessitate re-sticking the patient. To ensure sterility, re-sticking the patient requires the use of a new blood receptacle assembly, therefore increasing the initial cost the blood drawing procedure. Additionally, many patients who undergo multiple blood drawings have poor veins, increasing the difficulty of finding a suitable vein to use for blood sampling.

There is therefore a need for an improved blood sampling device which will permit blood samples to be taken with a conventional blood receptacle assembly, such as a "VACUTAINER," while providing increased stability, ease of use, safety and convenience for the blood drawing procedure. Further, there is a need for automating the blood taking procedure to permit multiple blood samples to be taken from a patient with increased stability, safety and convenience.

SUMMARY AND OBJECTS OF THE INVENTION

It is an object of the present invention to provide a simple, effective, and efficient apparatus for taking a blood sample or multiple blood samples from a patient.

In accordance with the present invention, a blood drawing device is provided for use with a blood receptacle assembly including a first part and second part, blood from a patient passing through the first part into the second part for collection therein, the device including a base, a mechanism secured to a base for securing the first part of the blood receptacle assembly, a mechanism for grasping the second part of the blood receptacle assembly, and a mechanism for moving the second part into engagement with the first part for collection of blood within the second part.

The mechanism for securing the first part of the blood receptacle assembly is preferably a holding element, the holding element preferably being u-shaped and having two oppositely situated pieces.

The mechanism for grasping the second part of the blood receptacle assembly preferably includes a clamping mechanism having two clamping elements, at least one of the clamping elements being configured for movement in a clamping direction to clamp the second part therebetween.

Preferably, the mechanism for moving the second part into engagement with the first part includes a connecting arm attached to a slide mechanism. Preferably, the device also includes a mechanism for manipulating the mechanism for grasping the mechanism for moving. The manipulating mechanism may comprise a lever attached to the connecting arm.

In accordance with another aspect of the invention, a blood drawing device is provided for use with a blood receptacle assembly including a first part and a second part, blood from a patient passing through the first part into the second part for collection therein, the device including a base having a surface, a holding element extending from the surface for securing the first part, a first grasping member extending from the surface, and a second grasping member and extending from the surface adjacent to the first grasping member. At least one of the first and second grasping members is movable in a grasping direction for grasping the second part of the blood drawing assembly between the first and second grasping members, both of the first and second grasping members being simultaneously movable toward the holding element to place the second part into engagement with the first part for collection of blood within the second part.

In accordance with yet another aspect of the invention, a blood drawing device is provided for use with a blood receptacle assembly including a first part and a second part, blood from a patient passing through the first part into the second part for collection therein, the blood drawing device including a base, a carriage assembly movably attached to the base and defining an opening for receiving the second part, a holding element fixed to the base and having an extending portion configured to receive the first part and secure the first part in a fixed location relative to the base, a mechanism for moving the carriage assembly relative to the base, and a mechanism for reciprocating the second part between a first and a second position relative to the carriage assembly within the opening, movement of the second part from the first position to the second position causing the second part to engage the first part to thereby permit collection of blood within the second part.

Preferably, the carriage assembly is a carousel, and the carousel rotates relative to the base.

The blood drawing device is preferably for use with a blood receptacle assembly including one first part and a plurality of second parts, the carriage defining a plurality of openings, each opening for receiving a given one of the second parts.

Optionally, a sensor for detecting a blood fill level within the second part may be provided, along with a valve operative responsive to the sensor detecting the blood fill level to preclude flow of blood to the first part. Also, responsive to the sensor detecting the blood fill level, the mechanism for reciprocating may retract the second part into the opening. Further, responsive to the sensor detecting the blood fill level, a moving mechanism may move the carriage assembly relative to the base. Preferably, the reciprocating mechanism includes a plurality of roller elements driven by a servo motor, and the roller elements include a first set of roller guides and a second set of roller guides spaced from the first set.

Additional objects and advantages of the invention will be set forth in part in the following description, or may be learned from practice of the invention.

BRIEF DESCRIPTION OF THE DRAWINGS

FIG. 6 is a partial cross-sectional view of the device of FIG. 1 taken along line 6—6 in FIG. 2a.

DESCRIPTION OF THE PREFERRED EMBODIMENTS

Figure 1:
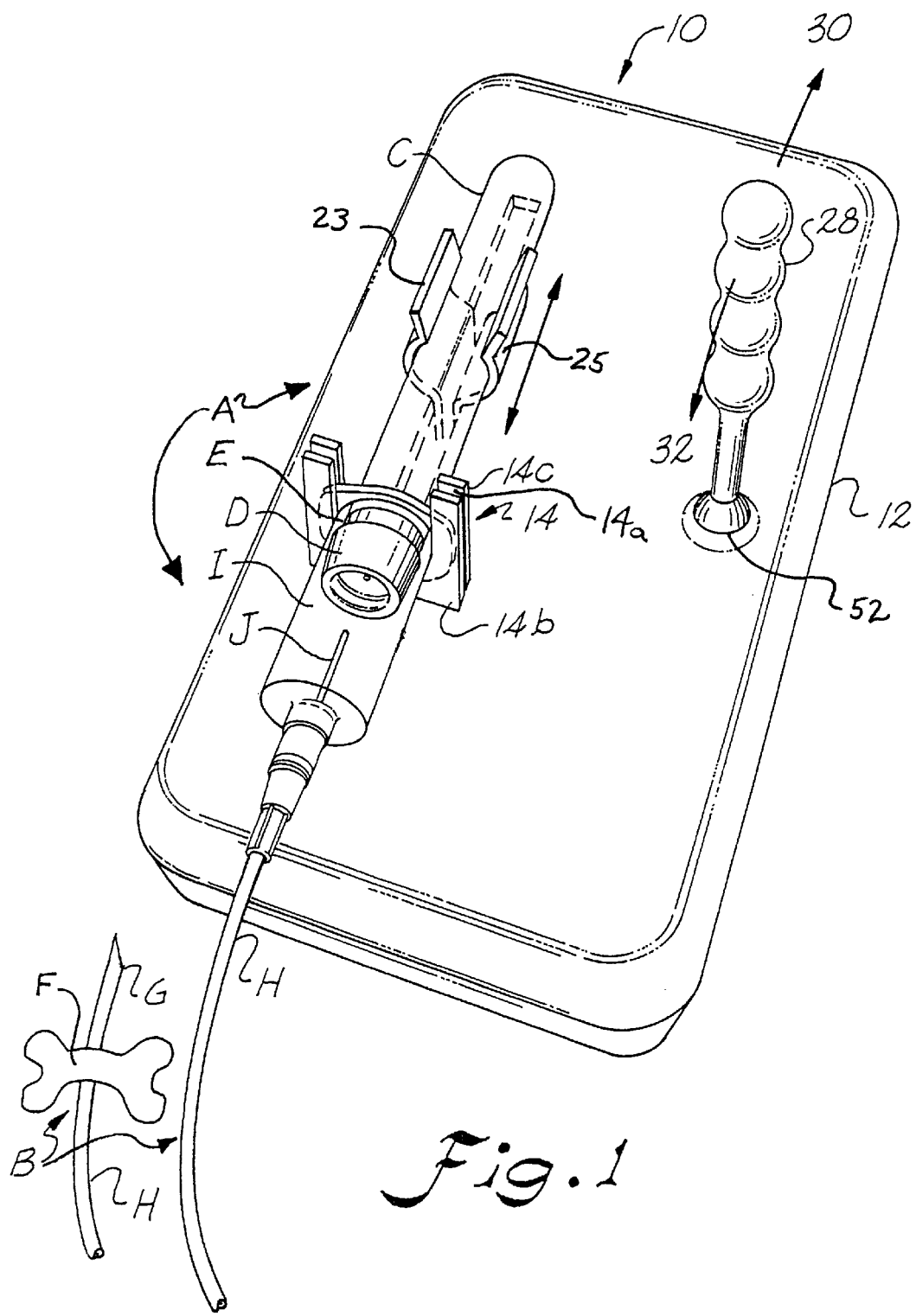
FIG. 1 is a perspective view of one embodiment of a blood sampling device according to the present invention.

Reference will now be made in detail to the presently preferred embodiments of the invention, one or more examples of which are illustrated in the drawings. Each example is provided by way of explanation of the invention, and not meant as a limitation of the invention. For example, features illustrated or described as part of one embodiment can be used on another embodiment to yield yet another embodiment. It is intended that the present invention include such modifications and variations.

FIG. 1 illustrates one embodiment of a blood drawing device 10 according to the present invention, along with conventional blood receptacle assembly A, as described above. Device 10 includes a base 12 and a means for securing a first part of the blood receptacle assembly A, namely blood collecting assembly B, to base 12. Base 12 may consist of metal, wood, plastic or any other suitable material and may further comprise a weighted base for increased stability.

As broadly embodied in FIG. 1, the means for securing includes a holding element such as u-shaped holder 14. The holding element may have various shapes in accordance with the invention, and such shapes are to a large part dependent on the design of the blood collecting assembly B. As shown in FIG. 1, u-shaped holder 14 may include two unitary, oppositely situated u-shaped pieces, first holder piece 14b and second holder piece 14c, positioned such that slot 14a is formed between first holder piece 14b and second holder piece 14c. A portion of housing I of blood collection assembly B slides into slot 14a, between holder piece 14b and holder piece 14c, thereby securing housing I during the blood drawing procedure and allowing for easy placement into and removal from holder 14.

In accordance with the invention, device 10 further includes a means for grasping the second part of the blood receptacle assembly A, namely tube C. As broadly embodied in FIGS. 1, 3, and 4, the means for grasping includes a clamping mechanism 20 including a first clamping element 23 and a second clamping element 25, which may also be referred to as grasping members. Preferably, at least one of clamping elements 23 and 25 is moveable in a clamping direction to clamp tube C between clamping elements 23 and 25. More preferably, both of clamping elements 23 and 25 are so moveable.

Figure 3:
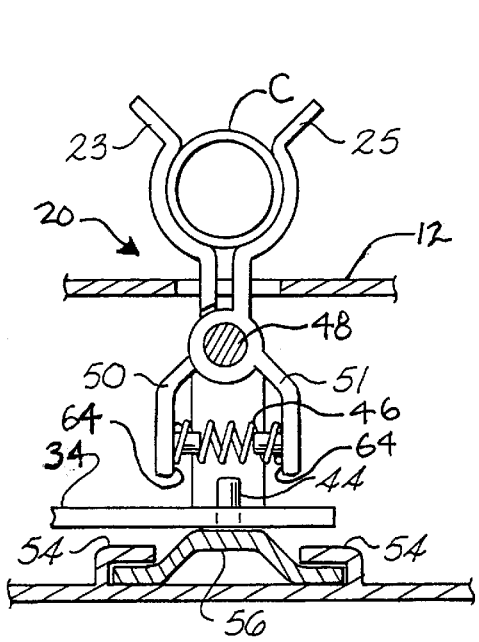
FIG. 3 is a partial cross-sectional view of the device of FIG. 1 taken along line 3—3 in FIG. 2a, showing a mechanism for grasping the second part of the blood receptacle assembly.
Figure 4:
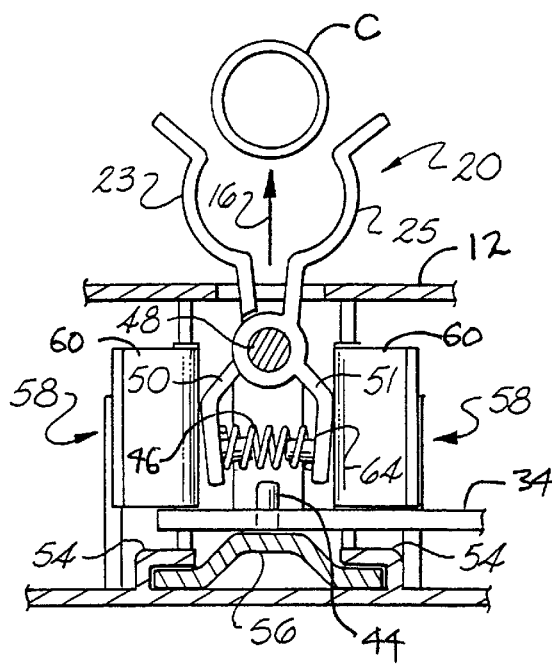
FIG. 4 is a partial cross-sectional view as in FIG. 3, showing the mechanism for grasping in a receiving position for receiving the second part of the blood receptacle assembly.

FIGS. 3 and 4 provide a cross-sectional view of clamping mechanism 20 in which both clamping elements 23 and 25 are pivotable about an axle 48. A compression spring 46 urges both of clamping elements 23 and 25 in the clamping direction, although it should be understood that only one of the clamping elements need be so moveable. Alternately, one of both of clamping elements 23 and 25 could be made flexible enough to permit insertion and removal of tube C, but firm enough to be able to move tube C into engagement with housing I, as will be described below.

FIG. 4 shows clamping elements 23 and 25 in an open position permitting blood sampling tube C to be inserted or removed as indicated by arrow 16. In the open position, compression spring 46 is compressed as leg 50 of clamping element 23 is moved closer to leg 51 of clamping element 25.

FIG. 3 shows clamping elements 23 and 25 in a clamped position in which they are grasping tube C. In such position, compression spring 46 causes tube C to be grasped securely between clamping elements 23 and 25.

Figure 2A:
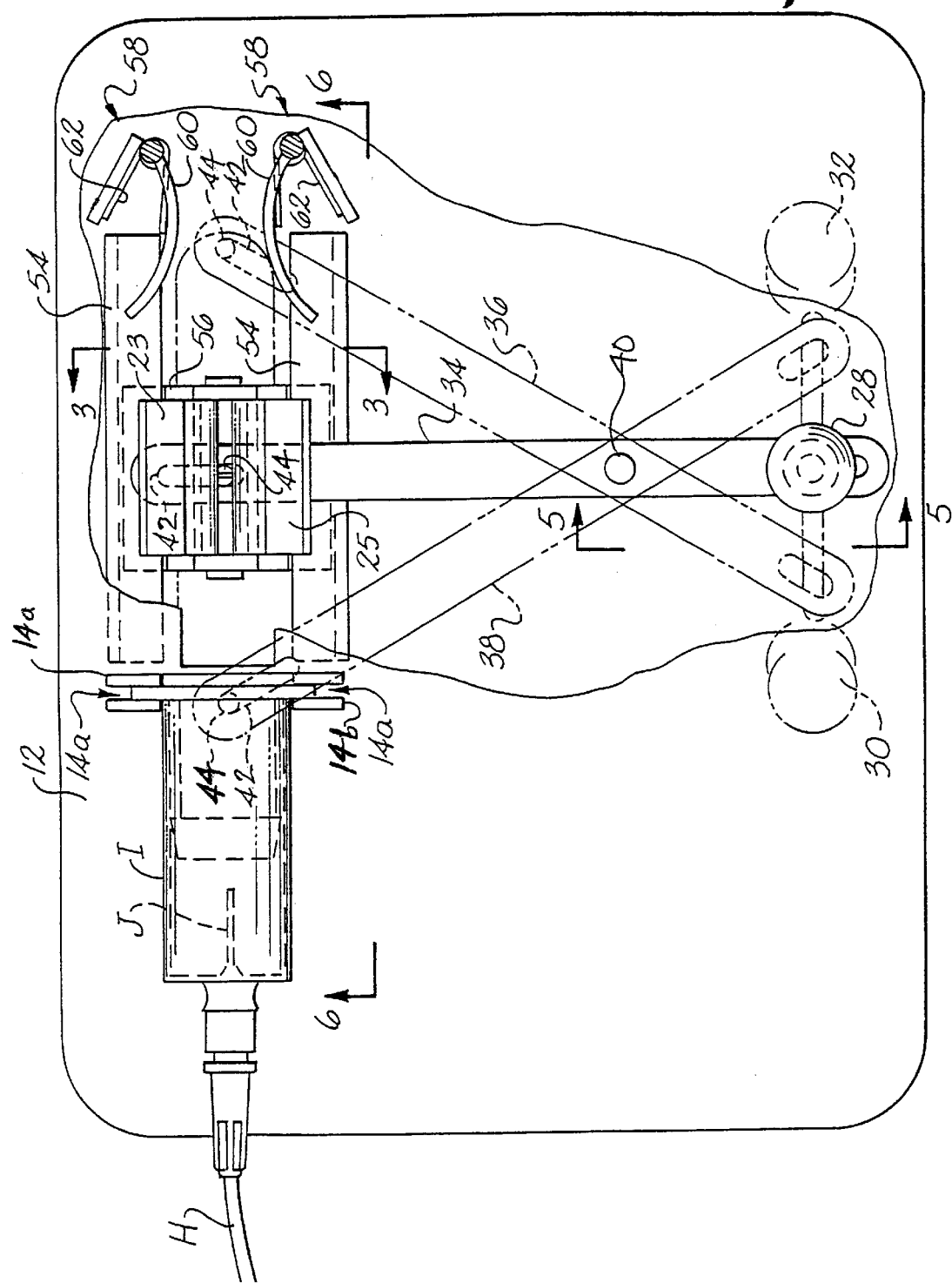
FIG. 2a is a top, cut-away view of the blood sampling device in FIG. 1.

According to the present invention, blood drawing device 10 further comprises a means for moving tube C of blood receptacle assembly A into engagement with blood collecting assembly B for collection of blood within tube C. FIG. 1 shows device 10 and tube C in position prior to such movement, and FIG. 2a shows device 10 and tube C after such movement. As indicated in FIG. 2a, such movement causes second needle J to puncture rubber stopper D of blood sampling tube C.

One such means for moving tube C into engagement with assembly B is broadly illustrated in FIG. 2a. As shown, the means for moving includes a connecting arm 34 attached to a slide mechanism 56 slidable along a track 54. Connecting arm 34 pivots on pin 40 between a first position 36 (in FIG. 2a and 2c) and a second position 38 (in FIG. 2a and 2b), as slide mechanism 56 slides along track 54. Arm 34 defines an elongated opening 42 for receiving a pin 44 extending from slide mechanism 56. Slide mechanism 56 thus slides back and forth within base 12 on track 54 as arm 34 pivots on pin 40.

Figure 5:
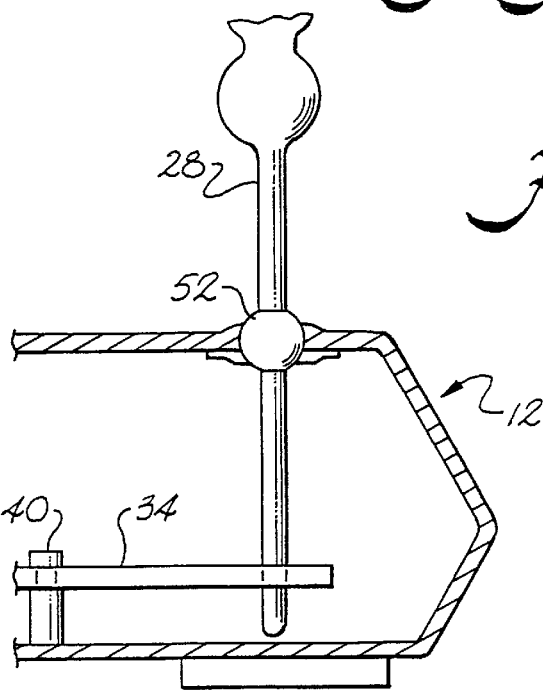
FIG. 5 is a partial cross-sectional view of the device of FIG. 1 taken along line 5—5 in FIG. 2a, showing the mechanism for moving the second part of the blood receptacle assembly into engagement with the first part of the blood receptacle assembly.
Figure 6:
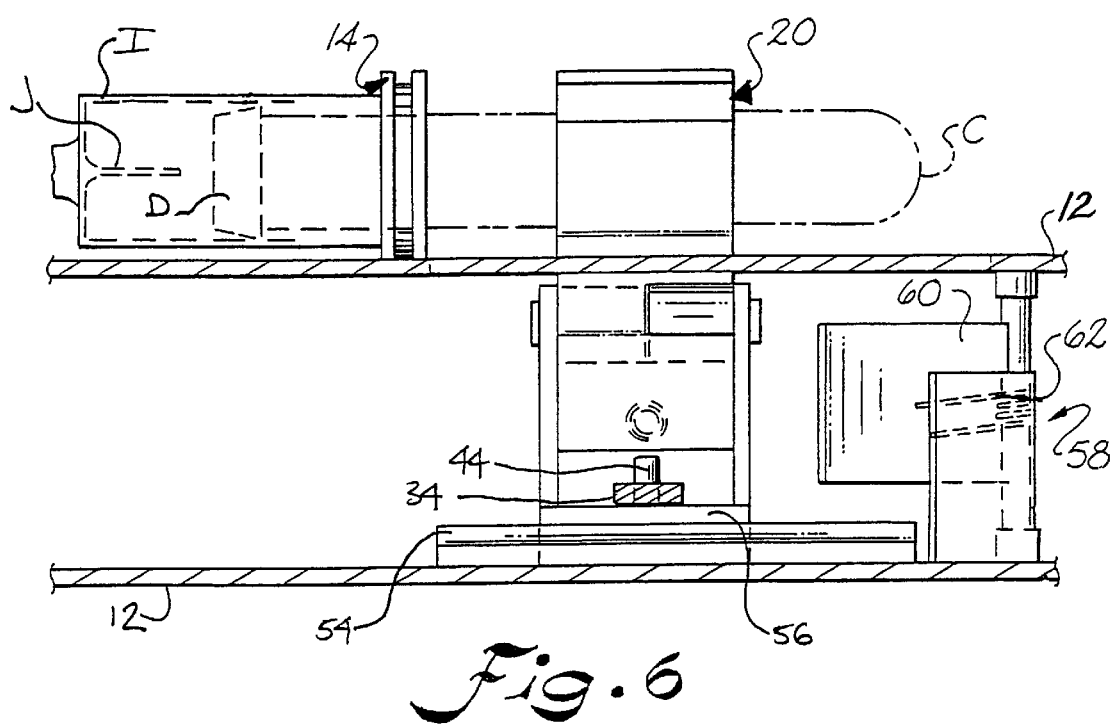

Preferably, device 10 further includes a means for manipulating the means for grasping and the means for moving. As broadly embodied in FIG. 2a and 5, the means for manipulating includes a lever 28 mounted to base 12 via a ball joint 52. Lever 28 is movable between first position 30 and second position 32 to thereby move connecting arm 34 between first position 36 and second position 38.

Figure 2B:
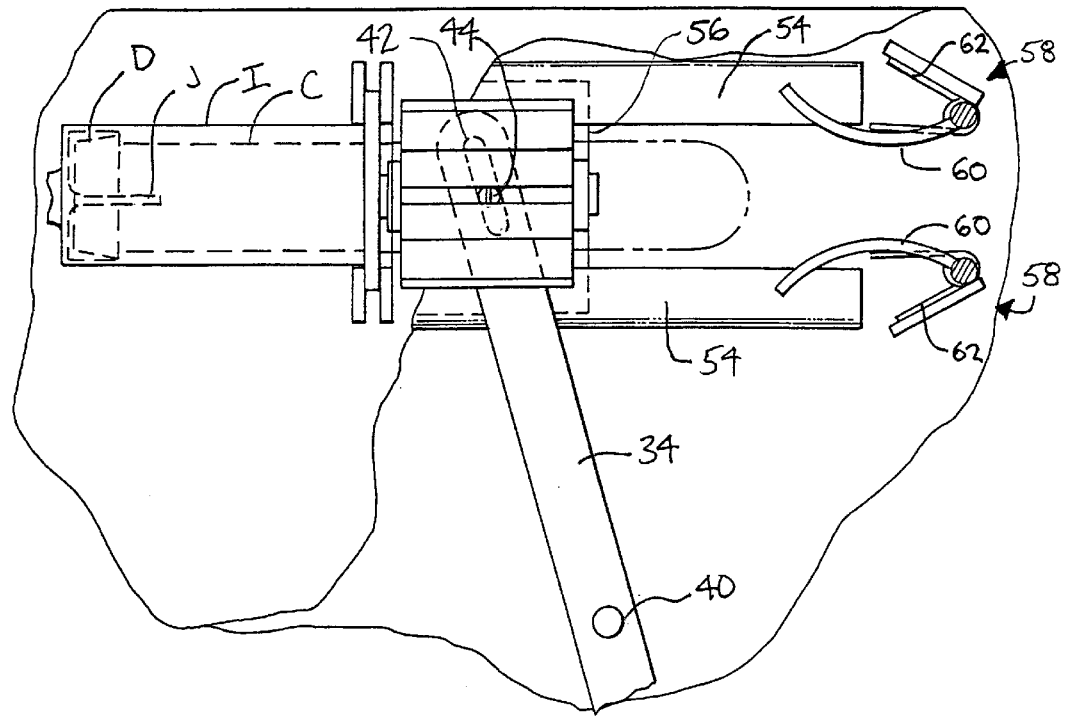
FIG. 2b is a partial cut-away view as in FIG. 2a showing the positioning of the device as the second part of the blood receptacle assembly engages the first part of the blood receptacle assembly.
Figure 2C:
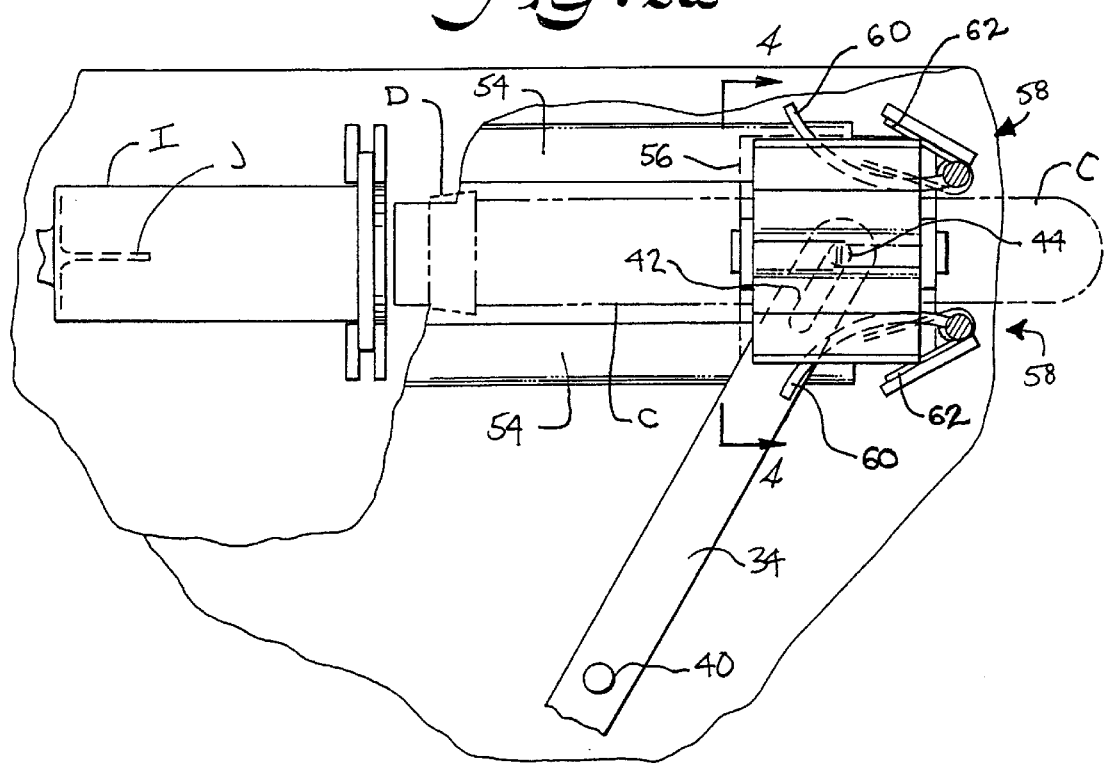
FIG. 2c is a partial cut-away view as in FIG. 2a showing positioning of the device as the second part of the blood receptacle assembly is disengaged from the first part of the blood receptacle assembly.

A clamp opening mechanism 58 is disposed at one end of track 54, as shown in FIG. 2a. Clamp opening mechanism 58 includes at least one gate 60 mounted with a torsion spring 62. FIGS. 3 and 4 illustrate clamping members 23 and 25 are mounted via axle 48 and arms 50 and 51 tensioned against a spring base 64 within base 12 to slide mechanism 56. When slide mechanism is slid from position shown in FIG. 2b to the position shown in FIG. 2c, gate(s) 60 contacts clamping members 23 and/or 25 to thereby open clamping mechanism 20. As shown in FIGS. 2b and 2c, two such gates and springs are provided, although only one gate and spring could be provided within the scope of the invention.

Thus, when lever 28 is in first position 30 and arm 34 is in first position 36, clamping members 23 and 25 are in the position shown in FIG. 4, and a tube may be readily placed into or removed from clamping mechanism 20. As lever 28 is moved toward position 32, arm 34 is moved toward position 38. Accordingly, clamping members 23 and 25 slide out of engagement with gates 60, thereby also clamping the clamping members around tube C to thereby firmly grasp the tube. As lever 28 is moved further toward position 32, clamping members 23 and 25 continue to slide tube C until stopper D moves into housing I to be pierced by needle J.

When lever 28 is moved in the opposite direction, slide mechanism 56 slides along track 54 in the opposite direction with clamping members 23 and 25 grasping tube C until clamping members 23 and 25 encounter gates 60. At that point, clamping members 23 and 25 open to the position shown in FIG. 4 allowing for removal of tube C and replacement if necessary.

This operation of device 10 provides a steady and reliable insertion and removal of tube C into housing I with second needle J that can be done with only one hand grasping device 10 (via lever 28) as long as base 12 is mounted in a steady location. Thus, use of device reduces the possibility of having movement of needle G in the patient's vein as compared with use of blood receptacle assembly A alone.

Figure 7:
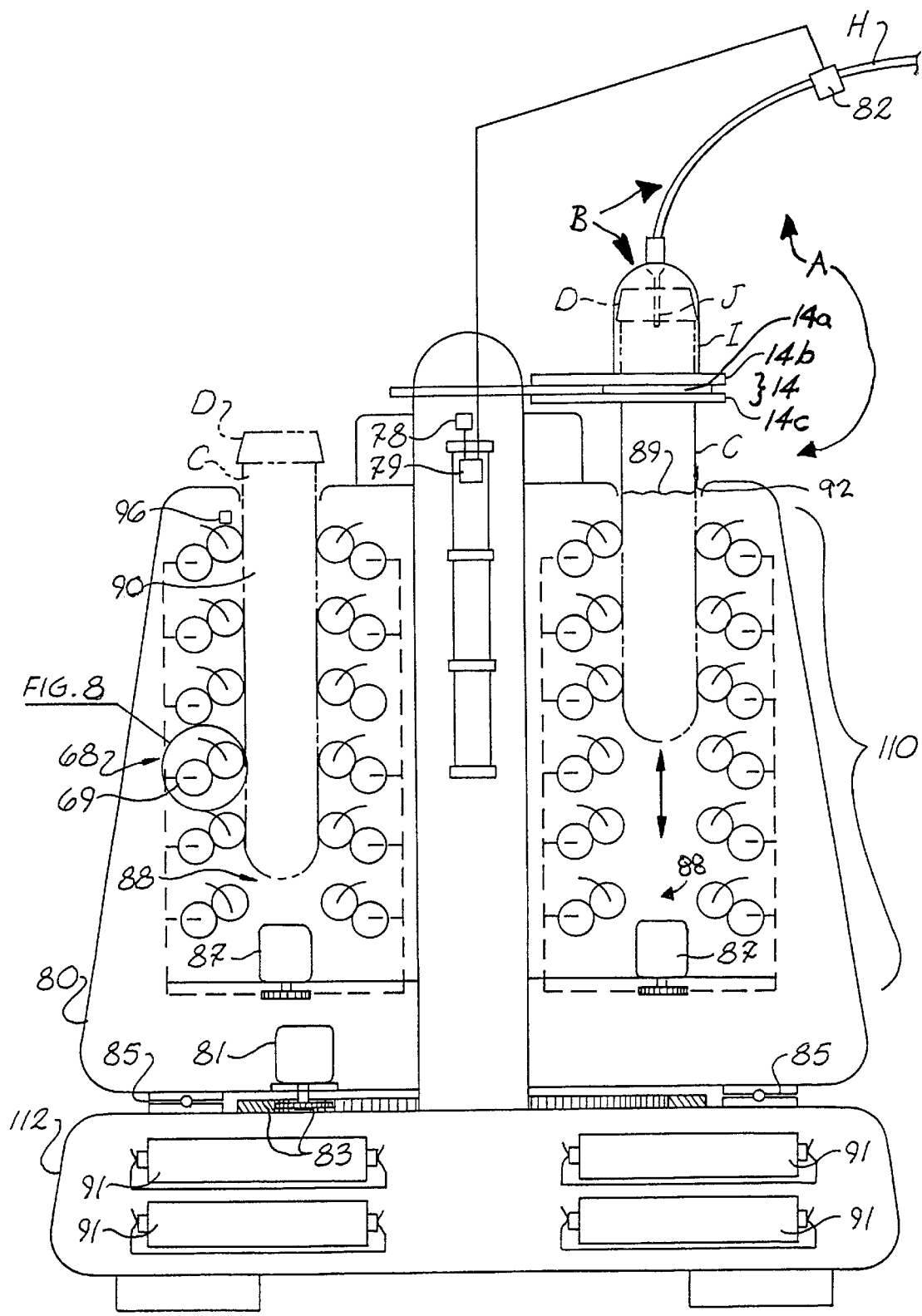
FIG. 7 is a schematic cross-sectional side view of a second embodiment of a blood sampling device according to the present invention.
Figure 8:
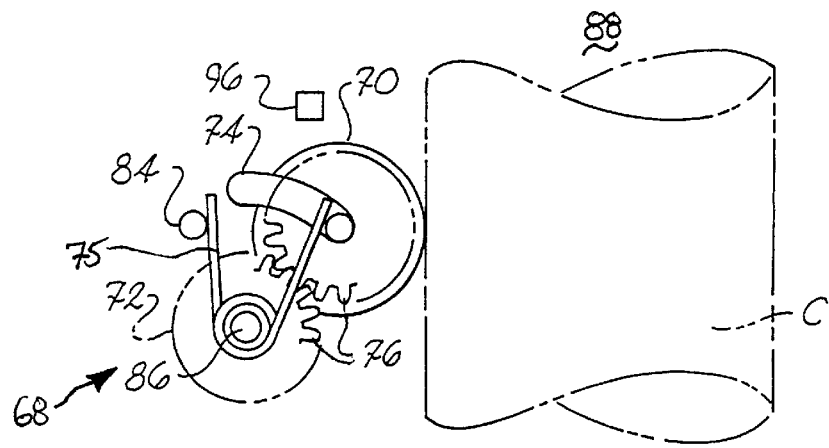
FIG. 8 is an enlarged view of the rollers shown in FIG. 7.
Figure 9:
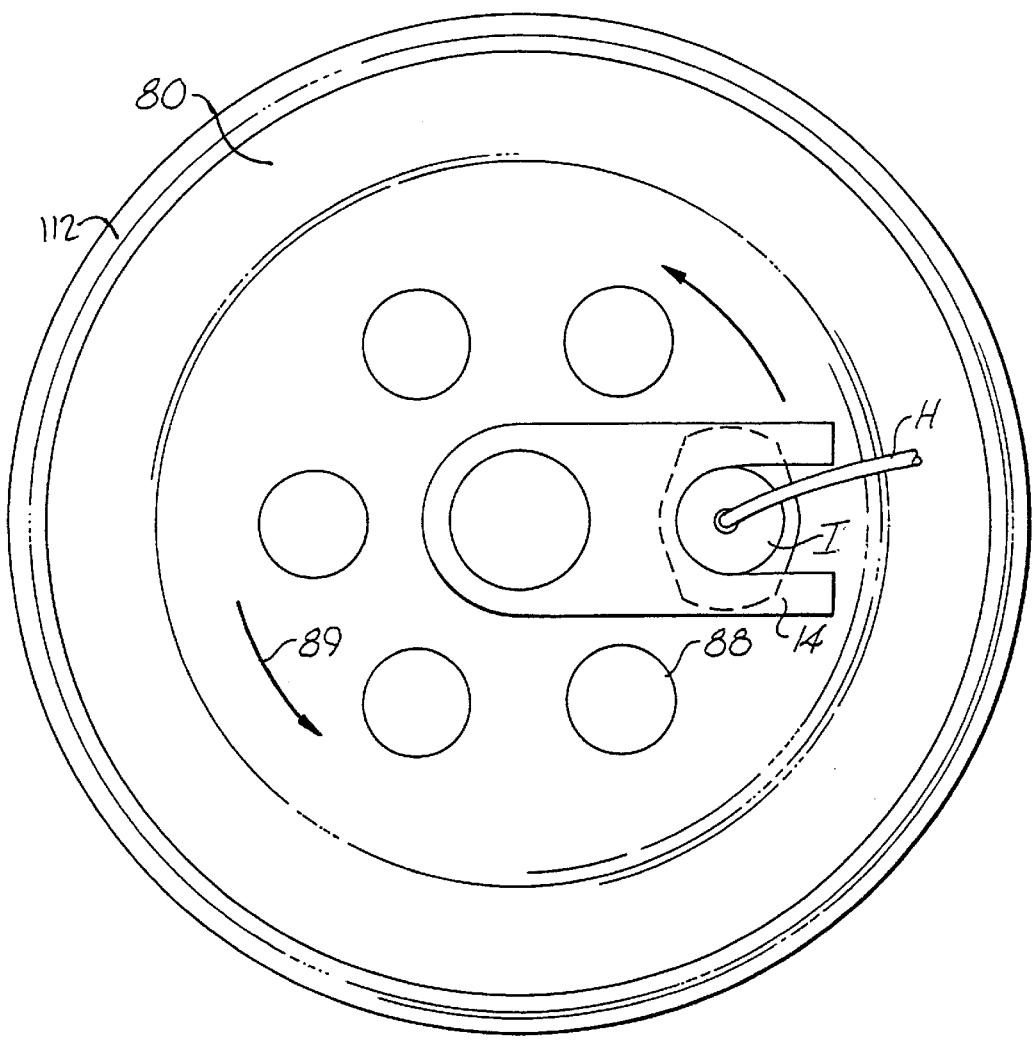
FIG. 9 is a top view of the embodiment of FIG. 7.

FIGS. 7–9 show an alternative embodiment of the blood drawing device of the present invention, along with conventional blood receptacle assembly A as described above. Where possible, common reference numerals have been used to identify elements of the second embodiment that are the same or substantially the same as elements of the first embodiment. As broadly embodied in FIG. 7, blood drawing device 110 includes a base 112; a carriage assembly 80 movably attached to base 112 and defining at least one opening 88 for receiving at least one blood sampling tube C, and a holding element 14 for securing the first part of blood receptacle assembly. Base 112 may consist of metal, wood, plastic or any other suitable material and may be weighted for increased stability.

As illustrated in FIG. 7, holding element 14 may have various shapes in accordance with the invention, and such shapes are to a large part dependent on the design of the blood collecting assembly B. As shown, holding element 14 in FIG. 7 is substantially the same as that of FIG. 1.

In accordance with the present invention, carriage assembly 80 preferably is a rotatable carousel; however, it should be noted that other arrangements are contemplated by the present invention. For instance, carriage assembly 80 may be configured in a linear arrangement such that movement of blood sampling tubes C occurs in a linear fashion.

In accordance with the invention, device 110 further includes a means for moving carriage assembly 80 relative to base 112, preferably such that carriage assembly 80 rotates relative to base 112, thus allowing for sequentially presenting multiple blood sampling tubes C for filling. One means for moving carriage assembly 80 relative to base 112 may include a servo motor 81, gearing 83, and roller bearings 85, as indicated in FIG. 7. It should be understood, however, that any suitable means for moving could be employed in the present invention and that the disclosed elements and their locations on carriage assembly 80 and base 112 are provided for exemplary purposes only.

In accordance with the invention, device 110 further includes a means for reciprocating blood sampling tube C between a first position 90 and a second position 92, such that when blood sampling tube C is in first position 90, blood sampling tube C is engaged with needle J through rubber stopper D permitting the collection of blood within tube C. One embodiment of a reciprocating means broadly illustrated in FIG. 7 includes a roller assembly 68, including a plurality of rollers 69 arranged circumferentially around opening 88. Preferably the roller elements include a first set of roller guides and a second set of roller guides spaced from the first set. However, as can be appreciated by one of skill in the art, the number and arrangement of roller guides is dependant upon the size of the tube used and similar facts and thus the embodiment illustrated in FIG. 7 is provided by way of explanation of the invention and not meant as a limitation.

An exploded view of roller assembly 68 is shown in FIG. 8. Roller assembly 68 includes a first gear 70, a second gear 72, slotted opening 74, and torsion spring 75. Torsion spring 75 urges first gear 70 along slot 74 toward the center of opening 88. A drive mechanism, such as one or more servo motors 87, may be utilized to drive first gears 70 via second gears 72 and gear teeth 76, as indicated in FIG. 7. Upon activation of the drive mechanism when tube C is in first position 90, the tube is thus moved from first position 90 to second position 92 by the interaction of gear teeth 76 on first gear 70 and second gear 72. The movement of blood sampling tube C from first reciprocating position 90 to second reciprocating position 92 permits blood sampling tube C to engage second needle J. The reverse operation of drive mechanism and the above associated parts moves tube C from second position 92 to first position 90.

In accordance with another aspect of the invention, a sensor 78 may be incorporated in blood sampling device 110. As shown in FIG. 7, one example of a suitable sensor 78 is an optical sensor which optically detects a blood fill level 89 in tube C. However, an optical sensor is only one type of sensor which may be suitable for use with the present invention. One of skill in the art would recognize that other types of sensors may be suitable for sensing desired blood fill level and thus can be employed in the present invention. A switch may be employed, either for use with or without connection to sensor 78, to operate device 110, as will be described below.

As broadly embodied in FIG. 7 and 8, device 110 may further include a sensor 96. Preferably sensor 96 may be connected to first roller 70 as shown in FIG. 8. As sensor 96 detects the insertion of tube C into opening 88, servo motor 87 is activated to move tube C from second reciprocating position 92 to first reciprocating position 90, thus permitting tube C to be lowered into opening 88.

Device 110 may also cause clamp 82 to clamp flexible tubing H so that blood collection into tube C is halted responsive to a signal from sensor 78. Clamp 82 is one embodiment of a means for interrupting blood flow. One of skill in the art will recognize that other mechanisms for interrupting blood flow may be suitable for use in the present invention, including valves, stopcocks and the like.

Device 110 may further include a connection between sensor 78 and the means for reciprocating blood tube C from first position 90 to second position 92, and the means for moving carriage assembly 80, both means being activated upon the sensing by sensor 78 of a blood fill level.

Device 110 may be powered by batteries 91, as shown, to provide portability. Alternately, device 110 could be powered by connection to any other suitable power source. Blood sampling device 110 operates as follows: Initially, at least one empty blood sampling tube C is in first position 90 within opening 88, wherein blood tube C is disengaged from second needle J. Upon actuation of switch 79, servo motor 87 and roller assembly 68 are activated, moving an empty blood tube C from first position 90 into second position 92 and thus into engagement with second needle J through stopper D. Blood flow from the patient enters needle G and travels via flexible tubing H through second needle J and into tube C for collection. Once the desired blood fill level is detected by sensor 78, blood flow through flexible tubing H is interrupted by clamp 82, and sensor 78 reactivates roller assembly 68, moving blood sampling tube C back into first position 90 and thus disengaging tube C from second needle J. Once blood sampling tube C is moved into first position 90, carriage assembly 80 is advanced in direction 89 so that another tube opening 88 is aligned with holder 14 by servo motor 81. A blood sampling tube C from the other opening 88 is subsequently moved into second position 92, engaging blood sampling tube C with second needle J. In this manner, any number of blood sampling tubes may be automatically and sequentially filled with minimal attention to the tubes by the venipuncturist, thereby permitting the venipuncturist to stabilize first needle G in contact with patient's vein. Once the blood drawing procedure is completed, needle G is withdrawn from the patient's vein and the blood sampling tubes are removed from the carriage assembly for processing and analysis.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit of the scope of the present invention, which is set forth in the following claims. In addition, it should be understood that aspects of the various embodiments may be interchanged both in whole or in part. Therefore, the spirit and scope of the appended claims should not be limited to the description of the preferred embodiments contained therein.

We claim:

1. A blood drawing device for use with a blood receptacle assembly including a first part and a second part, blood from a patient passing through the first part into the second part for collection therein, the blood drawing device comprising:

a base;

a means secured to the base for securing the first part of the blood receptacle assembly;

a means secured to the base for grasping the second part of the blood receptacle assembly;

a means secured to the base for moving the second part into engagement with the first part for collection of blood within the second part; and a means for manipulating the means for grasping and for manipulating the means for moving, the means for manipulating including a lever actuatable between a first position and a second position, movement of the manipulating means from the first position to the second position causing the means for grasping to clamp the second part of the blood receptacle assembly.

2. The blood drawing device of claim 1, wherein said base further comprises a weighted base.

3. The blood drawing device of claim 1, wherein the means for grasping includes a clamping mechanism having two clamping elements, at least one of the clamping elements being configured for movement in a clamping direction to clamp the second part between the clamping elements.

4. The blood drawing device of claim 3, wherein the clamping mechanism further includes a compression spring for the urging at least one of the clamping elements in the clamping direction.

5. The blood drawing device of claim 1, wherein the means for securing the first part of the blood receptacle assembly includes a u-shaped holding element.

6. The blood drawing device of claim 5, wherein the u-shaped holding element further comprises two oppositely situated pieces.

7. The blood drawing device of claim 1, further including an opening mechanism configured for opening the means for grasping when the manipulating means is disposed in the first position.

8. The blood drawing device of claim 7, wherein the opening mechanism includes at least one gate for contacting and moving an element of the means for grasping when the manipulating means is in the first position.

9. A blood drawing device for use with a blood receptacle assembly including a first part and a second part, blood from a patient passing through the first part into the second part for collection therein, the blood drawing device comprising:

a base;

a holding element extending from the base for securing the first part;

a first grasping member unitary with and extending from the base; and a second grasping member unitary with and extending from the base adjacent to the first grasping member, at least one of the first and second grasping members being movable in a grasping direction for grasping the second part of the blood drawing assembly between the first and second grasping members, both of the first and second grasping members being simultaneously movable toward the holding element to place the second part into engagement with the first part for collection of blood within the second part.

10. The blood drawing device of claim 9, wherein the means for grasping further includes a clamping mechanism for engaging the second part of the blood receptacle assembly, the clamping mechanism means for moving at least one of the grasping members toward and away from the other.

11. The blood drawing device of claim 10, wherein said clamping mechanism further includes a compression spring for urging at least one of the grouping members away from the other.

12. The blood drawing device of claim 9, wherein the holding element further comprises a u-shaped holder.

13. The blood drawing device of claim 12, wherein the u-shaped holder further comprises two oppositely situated pieces.

14. The blood drawing device of claim 9, further including an opening mechanism configured for opening the means for grasping when the manipulating means is disposed in the first position.

15. The blood drawing device of claim 14, wherein the opening mechanism includes at least one gate for contacting and moving an element of the means for grasping when the manipulating means is in the first position.

16. A blood drawing device for use with a blood receptacle assembly including a first part and a second part, blood from a patient passing through the first part into the second part for collection therein, the blood drawing device comprising:
- a base;
- a carriage assembly moveably attached to said base and defining an opening for receiving the second part;
- a securing element fixed to said base and having an extending portion configured to receive the first part and secure the first part in a fixed location relative to said base;
- a moving means for moving said carriage assembly relative to said base;
- a means for reciprocating said second part between a first and a second position relative to said carriage assembly within said opening, movement of the second part from the first position to the second position causing the second part to engage the first part to thereby permit collection of blood within the second part; and
- a sensor for detecting a blood fill level within said second part.

17. A blood drawing device as in claim 16, wherein said carriage assembly is a carousel.

18. A blood drawing device as in claim 17, wherein said carousel rotates relative to said base.

19. A blood drawing device as in claim 16, wherein said blood drawing device is for use with a blood receptacle assembly including one first part and a plurality of second parts, said carriage defining a plurality of openings, each said opening for receiving a given one of said second parts.

20. A blood drawing device as in claim 16, comprising a valve operative responsive to said sensor detecting said blood fill level to preclude flow of blood to said first part.

21. A blood drawing device as in claim 20, wherein responsive to said sensor detecting said blood fill level, said means for reciprocating retracts said second part onto said opening.

22. A blood drawing device as in claim 20, wherein responsive to said sensor detecting said blood fill level, said moving means moves said carriage assembly relative to said base.

23. A blood drawing device as in claim 17, wherein said moving means includes a servo motor.

24. A blood drawing device as in claim 16, wherein said reciprocating means includes a plurality of roller elements driven by a servo motor.

25. A blood drawing device as in claim 24, wherein said roller elements include a first set of roller guides and a second set of roller guides spaced from said first set.

26. A blood drawing device for use with a blood receptacle assembly including a first part and a second part, blood from a patient passing through the first part into the second part for collection therein, the blood drawing device comprising:
- a base;
- a means secured to the base for securing the first part of the blood receptacle assembly;
- a means secured to the base for grasping the second part of the blood receptacle assembly;
- a means secured to the base for moving the second part into engagement with the first part for collection of blood within the second part; and
- a means for manipulating the means for grasping and for manipulating the means for moving, the means for manipulating including a lever actuatable between a first position and a second position, movement of the manipulating means from the first position to the second position causing the means for moving to move the second part into engagement with the first part.

27. The blood drawing device of claim 26, wherein the means for grasping includes a clamping mechanism having two clamping elements, at least one of the clamping elements being configured for movement in a clamping direction to clamp the second part between the clamping elements.

28. The blood drawing device of claim 27, wherein the clamping mechanism further includes a compression spring for the urging at least one of the clamping elements in the clamping direction.

29. The blood drawing device of claim 26, wherein the means for securing the first part of the blood receptacle assembly includes a u-shaped holding element.

30. The blood drawing device of claim 26, further including an opening mechanism configured for opening the means for grasping when the manipulating means is disposed in the first position.

31. The blood drawing device of claim 30, wherein the opening mechanism includes at least one gate for contacting and moving an element of the means for grasping when the manipulating means is in the first position.

* * * * *